(12) United States Patent
Frey et al.

(10) Patent No.: US 6,315,773 B1
(45) Date of Patent: *Nov. 13, 2001

(54) EYE MOVEMENT SENSING SYSTEM

(75) Inventors: Rudolph W. Frey; John E. McWhirter, both of Orlando; Neil Zepkin, Casselberry; George Richard Downes, Jr., Orlando, all of FL (US)

(73) Assignee: Autonomous Technologies Corporation, Orlando, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/854,870

(22) Filed: May 12, 1997

Related U.S. Application Data

(63) Continuation of application No. 08/232,990, filed on Apr. 25, 1994, now abandoned.

(51) Int. Cl.[7] .................................................. A61N 5/02
(52) U.S. Cl. .................................. 606/12; 606/4; 606/10; 600/585
(58) Field of Search ........................... 606/2, 3–6, 10–13; 600/585

(56) References Cited

U.S. PATENT DOCUMENTS

| | | |
|---|---|---|
| 3,712,716 | 1/1973 | Cornsweet et al. . |
| 4,069,823 | 1/1978 | Isakov et al. . |
| 4,438,765 | 3/1984 | Wilinsky . |
| 4,443,075 | 4/1984 | Crane . |
| 4,579,430 | 1/1986 | Billie . |
| 4,669,466 | 6/1987 | L'Esperance . |
| 4,702,245 | 10/1987 | Schroder et al. . |
| 4,718,418 | 1/1988 | L'Esperance, Jr. . |
| 4,721,379 | 1/1988 | L'Esperance . |
| 4,729,372 | 3/1988 | L'Esperance, Jr. . |
| 4,759,615 | * 7/1988 | Bainbridge et al. ................. 600/160 |
| 4,848,340 | 7/1989 | Bille et al. . |
| 4,881,808 | 11/1989 | Bille et al. . |
| 4,901,718 | 2/1990 | Bille et al. . |
| 4,941,093 | 7/1990 | Marshall et al. . |
| 4,972,836 | * 11/1990 | Schenck et al. ..................... 600/558 |
| 5,048,946 | 9/1991 | Sklar et al. . |

(List continued on next page.)

FOREIGN PATENT DOCUMENTS

| | | |
|---|---|---|
| 24 50 095 A1 | 4/1976 | (DE) . |
| 0 151 869 A2 | 8/1985 | (EP) . |
| 85/01869 | 5/1985 | (WO) . |
| 87/06478 | 11/1987 | (WO) . |
| 92/21999 | 12/1992 | (WO) . |
| 93/16631 | 9/1993 | (WO) . |

*Primary Examiner*—David M. Shay
(74) *Attorney, Agent, or Firm*—Allen, Dyer, Doppelt, Milbrath & Gilchrist, P.A.

(57) ABSTRACT

A method and system are provided for sensing eye motion, such as saccadic eye motion, in a non-intrusive fashion. An optical delivery arrangement converts a laser beam pulse into a plurality of light spots. The light spots are focused such that they are incident on a corresponding plurality of positions located on a boundary whose movement is coincident with that of eye motion. The boundary can be defined by two visually adjoining surfaces having different coefficients of reflection. Energy is reflected from each of the positions located on the boundary receiving the light spots. An optical receiving arrangement detects the reflected energy from each of the positions. Changes in reflected energy at one or more of the positions is indicative of eye motion.

10 Claims, 5 Drawing Sheets

U.S. PATENT DOCUMENTS

| | | |
|---|---|---|
| 5,057,102 | 10/1991 | Tomioka et al. . |
| 5,098,426 | 3/1992 | Sklar et al. . |
| 5,178,617 | 1/1993 | Kuizenga et al. . |
| 5,302,979 | 4/1994 | Maeda et al. . |
| 5,329,544 | 7/1994 | Shachrai et al. . |
| 5,331,131 | 7/1994 | Opdyke . |
| 5,345,281 | 9/1994 | Taboada et al. . |
| 5,350,374 | 9/1994 | Smith . |
| 5,410,376 | 4/1995 | Cornsweet et al. . |
| 5,632,742 * | 5/1997 | Frey et al. ............................ 606/2 |

* cited by examiner

EYE MOVEMENT SENSING SYSTEM

This application is a continuation of application Ser. No. 08/232,990 filed Apr. 25, 1994, now pending.

FIELD OF THE INVENTION

The invention relates generally to ophthalmic laser surgery, and more particularly to an eye movement sensing method and system for use in ophthalmic perception, diagnostics and surgical procedures.

BACKGROUND OF THE INVENTION

Ophthalmic perception, diagnostics and/or surgical procedures involve a variety of equipment such as frequency multiplied infrared lasers, solid state lasers, radio frequency energy sources and ultrasound systems, just to name a few. In each of these systems/procedures, knowledge and/or control of eye position and movement is critical.

For example, photorefractive keratectomy (PRK) is a procedure for laser correction of focusing deficiencies of the eye by modification of corneal curvature. PRK is distinct from the use of laser-based devices for more traditional ophthalmic surgical purposes, such as tissue cutting or thermal coagulation. PRK is generally accomplished by use of a 193 nanometer wavelength excimer laser beam that ablates away corneal tissue in a photo decomposition process. Most clinical work to this point has been done with a laser operating at a fluence level of 120–195 mJ/cm$^2$ and a pulse-repetition rate of approximately 5–10 Hz. The procedure has been referred to as "corneal sculpting."

Before sculpting of the cornea takes place, the epithelium or outer layer of the cornea is mechanically removed to expose Bowman's membrane on the anterior surface of the stroma. At this point, laser ablation at Bowman's layer can begin. An excimer laser beam is preferred for this procedure. The beam may be variably masked during the ablation to remove corneal tissue to varying depths as necessary for recontouring the anterior stroma. Afterward, the epithelium rapidly regrows and resurfaces the contoured area, resulting in ail optically correct (or much more nearly so) cornea. In some cases, a surface flap of the cornea is folded aside and the exposed surface of the cornea's stroma is ablated to the desired surface shape with the surface flap then being replaced.

Phototherapeutic keratectomy (PTK) is a procedure involving equipment functionally identical to the equipment required for PRK. The PTK procedure differs from PRK in that rather than reshaping the cornea, PTK uses the excimer laser to treat pathological superficial corneal dystrophies, which might otherwise require corneal transplants.

In both of these procedures, surgical errors due to eye position errors including both initial centration errosr between the eye and the surgical laser and/or subsequent movement caused by involuntary (saccadic) eye movement, head movement or surgical equipment movement may degrade the refractive outcome of the surgery. The movement or positioning error is critical since the treatment laser's effectiveness depends on its being centered on the patient's theoretical visual axis which, practically speaking, is approximately the center of the patient's pupil. However, this visual axis is difficult to determine due in part to residual eye movement and involuntary eye movement known as saccadic eye movement. Saccadic eye movement is high-speed movement (i.e., of very short duration, 10–20 milliseconds, and typically up to 1° of eye rotation) inherent in human vision and is used to provide dynamic scene images to the retina. Saccadic eye movement, while being small in amplitude, varies greatly from patient to patient due to psychological effects, body chemistry, surgical lighting conditions, etc.

One approach for dealing with eye position error is to try to eliminate it by using a grasping device or suction ring to physically hold the patient's eye stable during surgery. However, the intrusive nature of the suction ring may distort the eye's shape thereby affecting surgical precision. Further, since the suction ring is typically held by the surgeon, the surgeon's lower frequency but larger amplitude hand motions become a factor in surgical precision.

Another approach for dealing with eye position error is to non-intrusively sense this eye position. One sensing technique/system known in the prior art is the 1st and 4th Purkinje reflection tracker. The 1st and 4th Purkinje reflections refer to images based on the 1st Purkinje image which is the glint reflection off the front surface of the cornea and the 4th Purkinje image which is a reflection off the back of the eye's lens. This technique/system is used to track X-Y position of the eye. However, for certain corneal sculpting surgical procedures, the 1st Purkinje surface is ablated thereby rendering this technique/system ineffective for corneal sculpting.

SUMMARY OF THE INVENTION

Accordingly, it is an object of the present invention to provide a method and system for sensing eye position and movement.

Another object of the present invention is to provide a method and system for sensing eye position and movement in a non-intrusive fashion.

Still another object of the present invention is to provide a method and system for sensing saccadic eye movement.

A further object of the present invention is to provide a method and system for sensing eye position and movement as a tool in ophthalmic laser surgery to include corneal sculpting procedures.

Yet another object of the present invention is to provide a method and system for sensing eye position and movement that is surgically eye safe.

Other objects and advantages of the present invention will become more obvious hereinafter in the specification and drawings.

In accordance with the present invention, a method and system are provided for sensing eye movement. A light source generates a modulated light beam in the near infrared 900 nanometer wavelength region. An optical delivery arrangement converts each laser modulation interval into a plurality of light spots. The light spots are focused such that they are incident on a corresponding plurality of positions located on a boundary whose movement is coincident with that of eye movement. The boundary can be defined by two visually adjoining surfaces having different coefficients of reflection. The boundary can be a naturally occurring boundary (e.g., the iris/pupil boundary or the iris/sclera boundary) or a man-made boundary (e.g., an ink ring drawn, imprinted or placed on the eye or a reflection enhancing tack affixed to the eye). Energy is reflected from each of the positions located on the boundary receiving the light spots. An optical receiving arrangement detects the reflected energy from each of the positions. Changes in reflected energy at one or more of the positions is indicative of eye movement.

DETAILED DESCRIPTION OF THE INVENTION

Figure 1A:
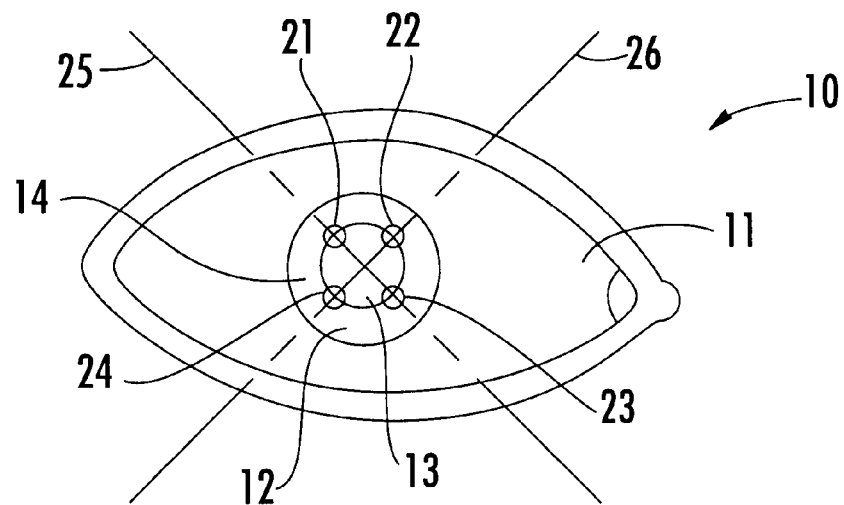
FIG. 1A is a plan view of an eye showing four light spots positioned on the eye's iris/pupil boundary in accordance with the present invention.

Referring now to the drawings, and more particularly to FIGS. 1A–1E, plan views of a human eye are shown and referenced generally by the numeral 10. From this planar perspective, eye 10 includes three visually adjoining surfaces, namely, a sclera or "white of the eye" 11, an iris 12 and a pupil 13. Each of sclera 11, iris 12, and pupil 13 has its own coefficient of reflection.

Figure 1B:
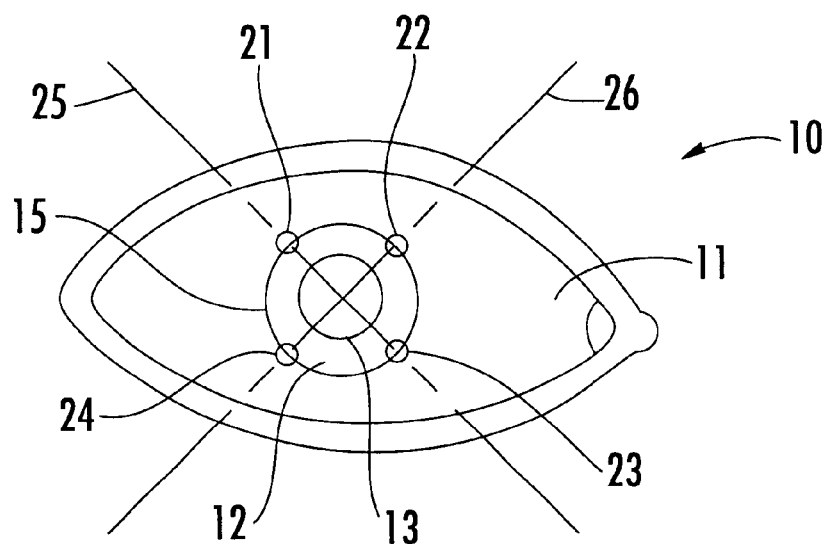
FIG. 1B is a plan view of an eye showing four light spots positioned on the eye's iris/sclera boundary.
Figure 1C:
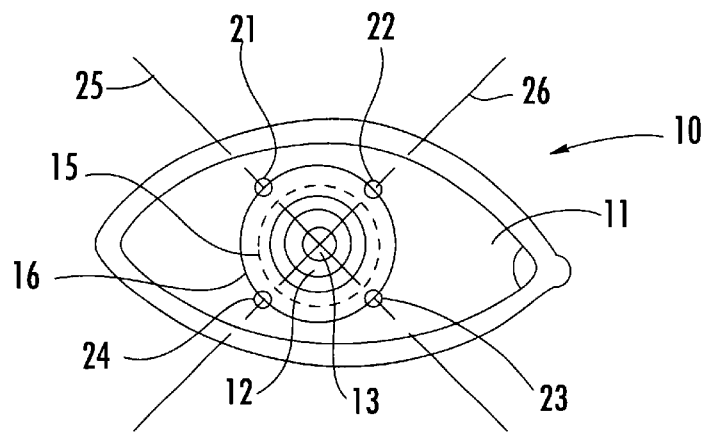
FIG. 1C is a plan view of an eye showing an ink ring affixed on the eye's iris/sclera boundary as well as four light spots positioned on the ink ring/sclera boundary.
Figure 1D:
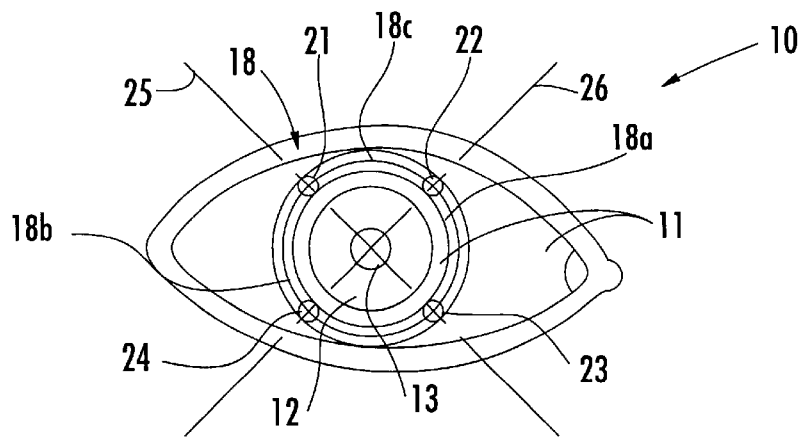
FIG. 1D is a plan view of an eye showing a double ink ring affixed on the eye's sclera as well as four light spots positioned on the boundary between the inner and outer ink rings of the double ink ring.
Figure 1E:
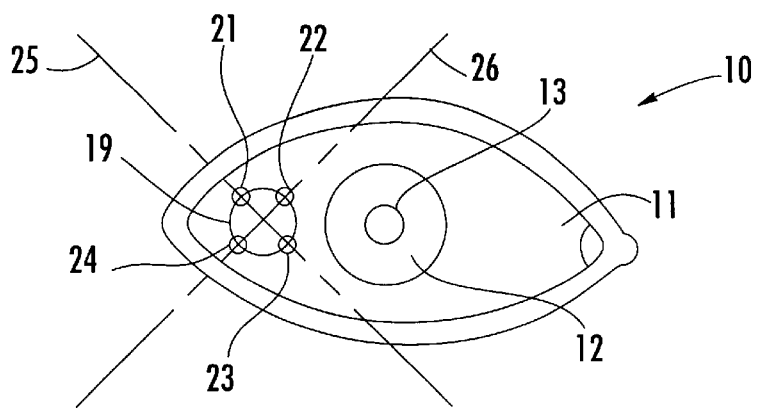
FIG. 1E is a plan view of an eye with a reflection enhancing tack affixed thereto and showing four light spots positioned on the boundary between the eye and the tack.

The method of the present invention is based on the preferable use of four spots of light, designated by circles 21, 22, 23 and 24. Spots 21 and 23 are positioned on axis 25 while spots 22 and 24 are positioned on axis 26 as shown. Axes 25 and 26 are orthogonal to one another. Spots 21, 22, 23 and 24 are focused to be incident on and evenly spaced about either the iris/pupil boundary 14 as shown in FIG. 1A or the iris/sclera boundary 15 as shown in FIG. 1B. In addition, man-made boundaries can be used. For example, as shown in FIG. 1C, an ink ring 16 can be placed on the iris/sclera boundary 15 to generate an ink ring/sclera boundary 17 that replaces or enhances boundary 15 in terms of its reflection differential with sclera 11. One ink that is commonly used for marking in ophthalmic procedures is a gentian violet colored ink available under the tradename "Visitec". As shown in FIG. 1D, a double ink ring 18 having an inner ink ring 18a with a first coefficient of reflection and an outer ink ring 18b with a second coefficient of reflection can be placed on sclera 11. Spots 21, 22, 23 and 24 are then positioned on orthogonal axes 25 and 26 on the boundary 18c between ink rings 18a and 18b. Another alternative is shown in FIG. 1E where a circular reflection enhancing tack 19 is affixed to some portion of eye 10 (e.g., sclera 11) and spots 21, 22, 23 and 24 are positioned on orthogonal axes 25 and 26 crossing at the center of tack 19.

In each of these cases, the operating principles are the same. The four spots 21, 22, 23 and 24 are of equal energy and are spaced evenly about and on the circular boundary of interest. This placement provides for two-axis motion sensing in the following manner. Each light spot 21, 22, 23 and 24 causes a certain amount of reflection at its position on the respective boundary. Since the respective boundary moves in coincidence with eye movement, the amount of reflection from light spots 21, 22, 23 and 24 changes in accordance with eye movement. By spacing the four spots evenly about the circular boundary geometry, horizontal or vertical eye movement is detected by changes in the amount of reflection from adjacent pairs of spots. For example, horizontal eye movement is monitored by comparing the combined reflection from light spots 21 and 24 with the combined reflection from light spots 22 and 23. In a similar fashion, vertical eye movement is monitored by comparing the combined reflection from light spots 21 and 22 with the combined reflection from light spots 23 and 24.

While the above described approach is the same for all cases shown in FIGS. 1A–1E, the remainder of the description will focus on the embodiment of FIG. 1A utilizing iris/pupil boundary 14. Utilizing iris/pupil boundary 14 is preferred because it is naturally occurring and because it presents the largest contrast in reflection characteristics. This is due mainly to the fact that pupil 13 reflects light directly back along its path of incidence while iris 12 reflects light back diffusely. Note that sclera 11 and ink ring 16 also reflect light diffusely with sclera 11 reflecting more than either iris 12 or ink ring 16. Accordingly, sclera 11 and iris 12 are used in combination (ie., iris/sclera boundary 15) and ink ring 16 can be used to replace or enhance iris/sclera boundary 15.

In view of the fact that the present invention is to be used in ophthalmic surgical procedures, the wavelength and power of light spots 21, 22, 23 and 24 must be taken into consideration. The light spots should preferably lie outside the visible spectrum so as not to interfere or obstruct a surgeon's view of the eye undergoing the surgical procedure. Further, the light spots must be "eye safe" to meet the American National Standards Institute (ANSI) safety requirements. While a variety of light wavelengths satisfy the above requirements, by way of example, light spots 21, 22, 23 and 24 are in the near infrared 900 nanometer wavelength mregion. Light in this region meets the above rated criteria and is further produced by readily available, economically affordable light sources. One such light source is a high pulse repetition rate GaAs 905 nanometer laser operating at 4 kHz which produces an ANSI defined eye safe pulse of 10 nanojoules in a 50 nanosecond pulse.

The size of spots 21, 22, 23 and 24 is varied in accordance with the boundary of interest. For example, spot size for use with iris/pupil boundary 14 is on the order of 1 millimeter while spot size for use with iris/sclera boundary 15 is on the order of 2 millimeters. However, it is to be understood that the size of the spots is not fixed and may indeed change with variations in patients and background illumination.

Figure 2:
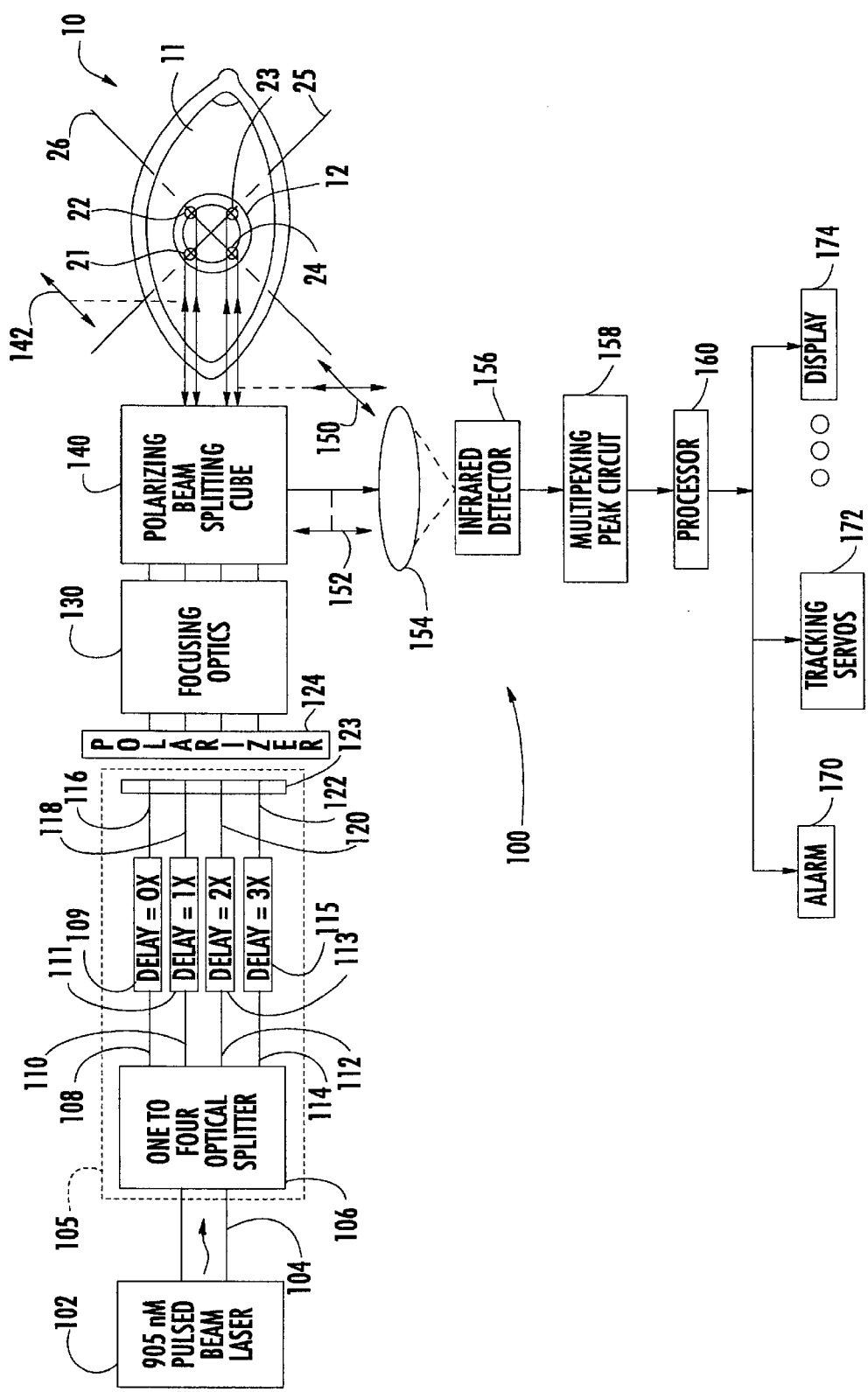
FIG. 2 is a block diagram of a preferred embodiment eye movement sensing system in accordance with the present invention.

A preferred embodiment system, referenced generally by numeral 100, for carrying out the method of the present invention will now be described with the aid of the block diagram shown in FIG. 2. System 100 may be broken down into a delivery portion and a receiving portion. Essentially, the delivery portion projects light spots 21, 22, 23 and 24 onto eye 10 as described above, while the receiving portion monitors reflections caused by light spots 21, 22 , 23 and 24.

The delivery portion includes a 905 nanometer pulsed diode laser 102 transmitting light through optical fiber 104 to an optical fiber assembly 105 that splits and delays each pulse from laser 102 into preferably four equal energy pulses. Assembly 105 includes one-to-four optical splitter 106 that outputs four pulses of equal energy into optical fibers 108, 110, 112, 114. Such optical splitters are commercially available (e.g., model HLS2X4 manufactured by Canstar and model MMSC-0404-0850-A-H-1 manufactured by E-Tek Dynamics). In order to use a single processor to process the reflections caused by each pulse transmitted by fibers 108, 110, 112 and 114, each pulse is uniquely multiplexed by a respective fiber optic delay line (or optical modulator) 109, 111, 113 and 115. For example, delay line 109 causes a delay of zero, i.e., DELAY=0x where x is the delay increment; delay line 111 causes a delay of x, i.e., DELAY=1x; etc.

The pulse repetition frequency and delay increment x are chosen so that the data rate of system 100 is greater than the speed of the movement of interest. In terms of saccadic eye movement, the data rate of system 100 must be on the order of at least several hundred hertz. For example, a system data rate of 4 kHz is achieved by 1) selecting a small but sufficient value for x to allow processor 160 to handle the data (e.g., 160 nanoseconds), and 2) selecting the time between pulses from laser 102 to be 250 microseconds (i.e., laser 102 is pulsed at a 4 kHz rate).

Figure 3:
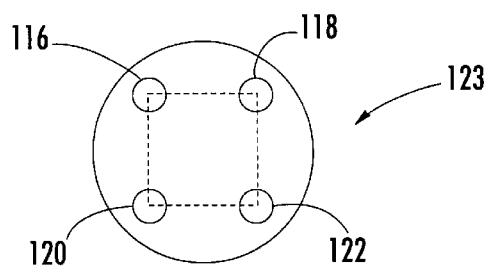
FIG. 3 is a cross-sectional view of the fiber optic bundle arrangement in FIG. 2.

The four equal energy pulses exit assembly 105 via optical fibers 116, 118, 120 and 122 which are configured as a fiber optic bundle 123. Bundle 123 arranges optical fibers 116, 118, 120 and 122 in a manner that produces a square (dotted line) with the center of each fiber at a corner thereof as shown in the cross-sectional view of FIG. 3. For sake of clarity, various well known structural features of bundle 123 (e.g., cladding on the fibers, spacers, insulation, etc.) have been omitted.

Light from assembly 105 is passed through an optical polarizer 124 that attenuates the vertical component of the light and outputs horizontally polarized light beams as indicated by arrow 126. Horizontally polarized light beams 126 pass to focusing optics 130 where spacing between beams 126 is adjusted based on the boundary of interest. Additionally, a zoom capability can be provided to allow for adjustment of the size of the pattern formed by spots 21, 22, 23 and 24. This capability allows system 100 to adapt to different patients, boundaries, etc.

Figure 4:
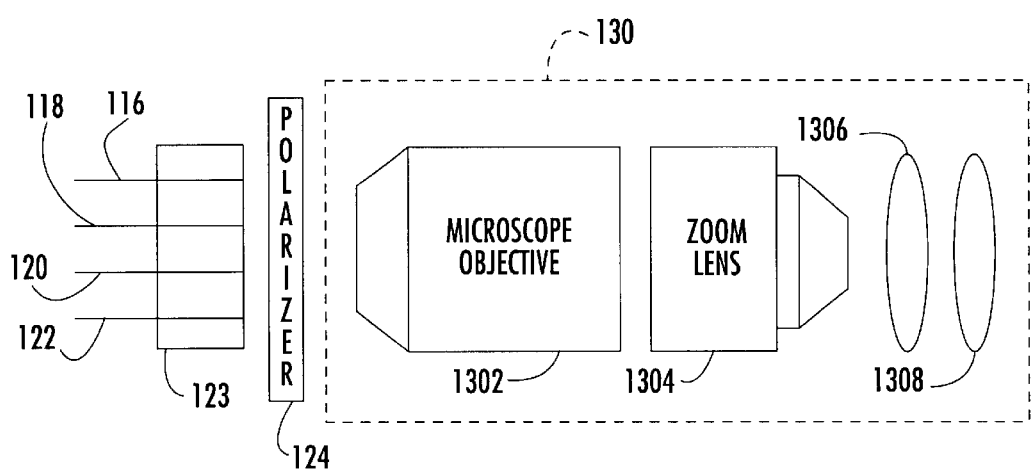
FIG. 4 is a block diagram of a preferred embodiment optical arrangement for the focusing optics in the delivery portion of the present invention.

While a variety of optical arrangements are possible for focusing optics 130, one such arrangement is shown by way of example in FIG. 4. In FIG. 4, fiber optic bundle 123 is positioned at the working distance of microscope objective 1302. The numerical aperture of microscope objective 1302 is selected to be equal to the numerical aperture of fibers 116, 118, 120 and 122. Microscope objective 1302 magnifies and collimates the incoming light. Zoom lens 1304 provides an additional magnification factor for further tunability. Collimating lens 1306 has a focal length that is equal to its distance from the image of zoom lens 1304 such that its output is collimated. The focal length of imaging lens 1308 is the distance to the eye such that imaging lens 1308 focuses the light as four sharp spots on the corneal surface of the eye.

Referring again to FIG. 2, polarizing beam splitting cube 140 receives horizontally polarized light beams 126 from focusing optics 130. Polarization beamsplitting cubes are well known in the art. By way of example, cube 140 is a model 10FC16PB.5 manufactured by Newport-Klinger. Cube 140 is configured to transmit only horizontal polarization and reflect vertical polarization. Accordingly, cube 140 transmits only horizontally polarized light beams 126 as indicated by arrow 142. Thus, it is only horizontally polarized light that is incident on eye 10 as spots 21, 22, 23 and 24. Upon reflection from eye 10, the light energy is depolarized (i.e., it has both horizontal and vertical polarization components) as indicated by crossed arrows 150. The vertical component of the reflected light is then directed/reflected as indicated by arrow 152. Thus, cube 140 serves to separate the transmitted light energy from the reflected light energy for accurate measurement.

The vertically polarized portion of the reflection from spots 21, 22, 23 and 24, is passed through focusing lens 154 for imaging onto an infrared detector 156. Detector 156 passes its signal to a multiplexing peak detecting circuit 158 which is essentially a peak sample and hold circuit, a variety of which are well known in the art. Circuit 158 is configured to sample (and hold the peak value from) detector 156 in accordance with the pulse repetition frequency of laser 102 and the delay x. For example, if the pulse repetition frequency of laser 102 is 4 kHz, circuit 158 gathers reflections from spots 21, 22, 23 and 24 every 250 microseconds.

Figure 5:
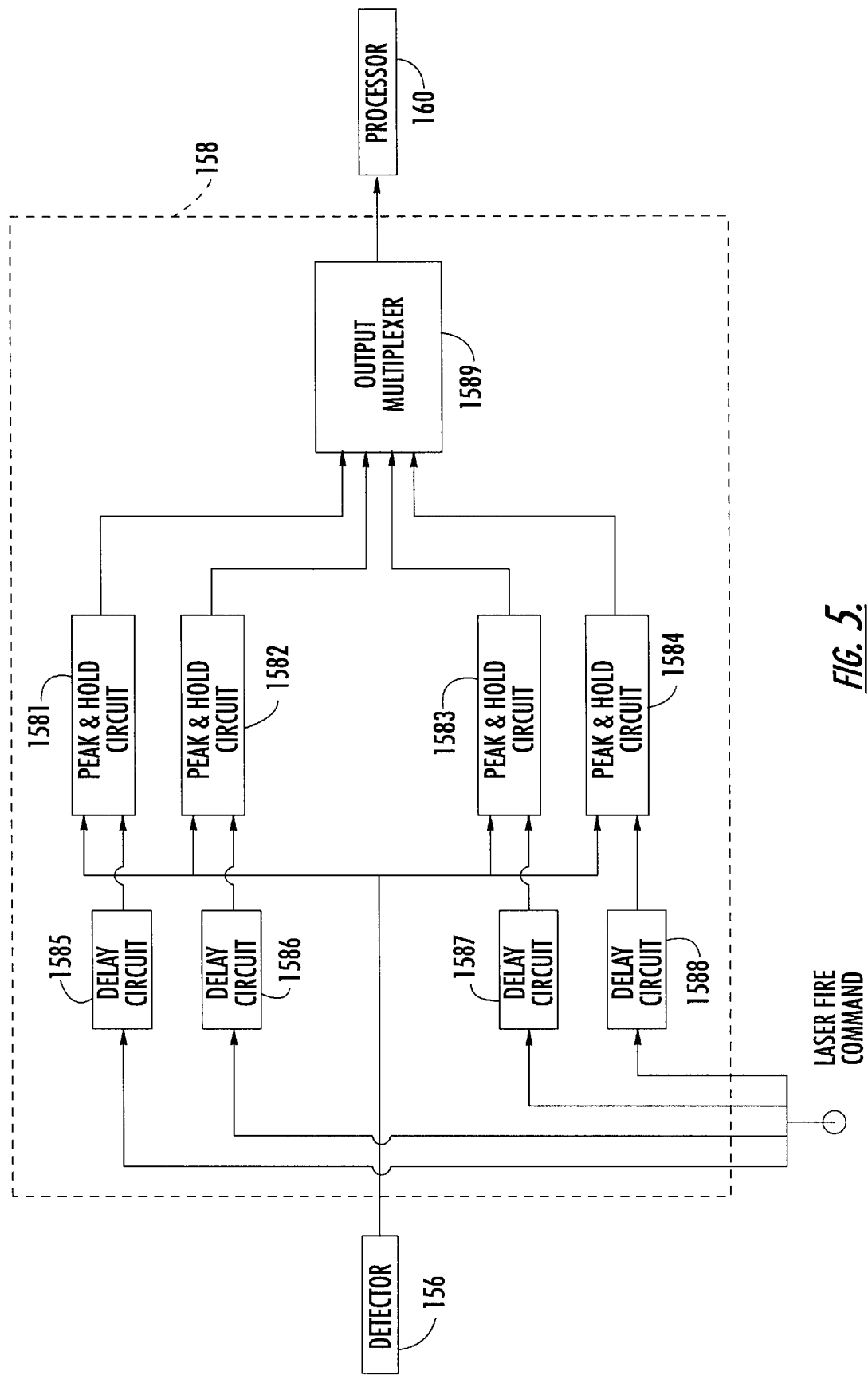
FIG. 5 is a block diagram of a representative multiplexing peak circuit shown in FIG. 2.

By way of example, infrared detector 156 ia an avalanche photodiode model C30916E manufactured by EG&G. A representative time multiplexing peak circuit 158 is shown in greater detail in the block diagram of FIG. 5. The detector signal output from detector 156 is input to four peak and hold circuits 1581, 1582, 1583 and 1584. For a given transmitted laser pulse, the detector output will consist of four pulses separated in time by the delays associated with optical delay lines 109, 111, 113 and 115 shown in FIG. 2. These four time separated pulses are fed to peak and hold circuits 1581, 1582, 1583 and 1584. Input enabling signals are also fed to the peak and hold circuits in synchronism with the laser fire command. The enabling signal for each peak and hold circuit is delayed by delay circuits 1585, 1586, 1587 and 1588. The delays are set to correspond to the delays of delay lines 109, 111, 113 and 115 to allow each of the four pulses to be input to the peak and hold circuits. For example, delay circuit 1585 causes a time delay of zero corresponding to delay line 109, delay circuit 1586 causes a time delay of x corresponding to delay line 111, etc. Thus, the reflected energy associated with a group of four spots is collected as the detector signal is acquired by all four peak and hold circuits 1581, 1582, 1583 and 1584. At this point, output multiplexer 1589 reads the value held by each peak and hold circuit and inputs them sequentially to processor 160.

The values associated with the reflected energy for each group of four spots (i.e., each pulse of laser 102) passed to a processor 160 are used to determine the horizontal and vertical components of eye movement. For example let $R_{21}$, $R_{22}$, $R_{23}$ and $R_{24}$ represent the detected amount of reflection from one group of spots 21, 22, 23 and 24, respectively. A quantitative amount of horizontal movement is determined directly from the normalized relationship $$\frac{(R_{21} + R_{24}) - (R_{22} + R_{23})}{R_{21} + R_{22} + R_{23} + R_{24}} \qquad (1)$$

while a quantitative amount of vertical movement is determined directly from the normalized relationship $$\frac{(R_{21} + R_{22}) - (R_{23} + R_{24})}{R_{21} + R_{22} + R_{23} + R_{24}} \qquad (2)$$

Note that normalizing (i.e., dividing by $R_{21}+R_{22}+R_{23}+R_{24}$) reduces the effects of variations in signal strength.

Once processed, the reflection differentials indicating eye movement (or the lack thereof) can be used in a variety of ways. For example, an excessive amount of eye movement may be used to trigger an alarm 170. In addition, the reflection differential may be used as a feedback control for tracking servos 172 used to position an ablation laser. Still further, the reflection differentials can be displayed on display 174 for monitoring or teaching purposes.

The advantages of the present invention are numerous. Eye movement is sensed in accordance with a non-intrusive method and apparatus. The present invention will find great utility in a variety of ophthalmic surgical procedures without any detrimental effects to the eye or interruption of a surgeon's view. Further, data rates needed to sense saccadic eye movement are easily and economically achieved.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. A system for sensing eye movement, the system comprising:

a light source providing a pulsed light beam;

an optical delivery arrangement operable with said light source for converting each pulse of said pulsed light beam into a plurality of light spots and for focusing said plurality of light spots to be incident on a corresponding plurality of positions located on a boundary whose movement is coincident with that of said eye movement, said boundary defined by two visually adjoining surfaces of the eye having different coefficients of reflection, wherein energy is reflected from each of said plurality of positions; and an optical receiving arrangement for detecting said reflected energy from each of said plurality of positions, wherein changes in said reflected energy at one or more of said positions is indicative of eye movement.

2. A system as in claim 1, wherein each of said plurality of light spots has a wavelength of approximately 900 nanometers.

3. A system as in claim 1, wherein said optical delivery arrangement includes zoom optics for adjusting the size of a pattern formed by said plurality of light spots incident on said corresponding plurality of positions.

4. A system as in claim 1, wherein said delay means comprises fiber optic delay lines.

5. An eye movement sensing system comprising:

a single light source for generating a light beam;

an optical delivery arrangement operable with said single light source for converting said light beam into a plurality of separate light sources and for directing said plurality of separate light sources onto a corresponding plurality of positions as a plurality of separate spots located on a surface of an eye, wherein the surface reflects light energy from said plurality of spots with the amount of said energy changing with eye movement, said optical delivery arrangement including delay means for introducing a unique time delay and for providing a unique identification for each of said plurality of separate spots; and an optical receiving arrangement for detecting said light energy from each of said plurality of spots reflected from the surface of the eye, wherein changes in said reflected energy from said plurality of separate spots is representative of the eye movement.

6. A system for sensing eye movement, the system comprising:

a light source for generating a pulsed light beam;

an optical delivery arrangement operable with said light source for converting each pulse of said pulsed light beam into a plurality of light spots and for focusing said plurality of light spots to be incident on a corresponding plurality of positions located on a boundary whose movement is coincident with that of said eye movement, said boundary defined by two visually adjoining surfaces of the eye having different coefficients of reflection, wherein energy is reflected from each of said plurality of positions;

an optical receiving arrangement for detecting said reflected energy from each of said plurality of positions, wherein changes in said reflected energy at one or more of said positions is indicative of eye movement; and means for polarizing each of said plurality of equal energy pulses into horizontally polarized components, said optical delivery arrangement including a polarization beam splitting cube for transmitting only said horizontally polarized components from each of said plurality of equal energy pulses forming said plurality of light spots.

7. A system as in claim 6, wherein said reflected energy from each of said plurality of positions is vertically and horizontally polarized, said optical receiving arrangement comprising:

said polarization beam splitting cube for directing said reflected energy that is vertically polarized separately from said reflected energy that is horizontally polarized; and energy detecting optics for measuring said reflected energy that is vertically polarized.

8. A system as in claim 7, wherein each of said plurality of light spots has a wavelength of approximately 900 nanometers, and wherein said energy detecting optics includes an infrared detector.

9. A system as in claim 8, wherein said wavelength is 905 nanometers.

10. An eye movement sensing system comprising:

light transmitting means for transmitting a plurality of pulsed light beams to spaced light spots at selected positions on a surface of an eye, each of said plurality of pulsed light beams having an identifiable time delay for delivery of the pulsed light beam to the selected position;

polarizing means operable with said light transmitting means for intercepting said plurality of pulsed light beams and polarizing each light pulse and delivering polarized light pulses having a first polarizing direction, said polarizing means positioned for receiving reflected light pulses returning from the eye and polarizing the reflected light into a second polarizing direction; and detecting means receiving the reflected light polarized in the second polarizing direction, the transmitted light thus being separated from the reflected light, said detecting means detecting changes in the reflected light from each of the plurality of spaced light spots at the selected positions, wherein the changes provide an indication of eye movement.

* * * * *